United States Patent [19]

Schneider

[11] Patent Number: 4,889,124
[45] Date of Patent: Dec. 26, 1989

[54] BIOMAGNETIC MEASURING INSTALLATION

[75] Inventor: Siegfried Schneider, Erlangen, Fed. Rep. of Germany

[73] Assignee: Siemens Aktiengesellschaft, Berlin and Munich, Fed. Rep. of Germany

[21] Appl. No.: 130,026

[22] Filed: Dec. 8, 1987

[30] Foreign Application Priority Data

Dec. 9, 1986 [DE] Fed. Rep. of Germany ....... 3641934

[51] Int. Cl.$^4$ ................................................. A61B 5/05
[52] U.S. Cl. .................................................... 128/653
[58] Field of Search ............................ 128/653; 52/167

[56] References Cited

U.S. PATENT DOCUMENTS 3,557,777 1/1971 Cohen ................................. 128/653

OTHER PUBLICATIONS

"Design, Construction, and Performance of a Large-Volume Magnetic Shield," Kelha et al, IEEE Trans. Mag., vol. MAG-18, No. 1, Jan. 1982, pp. 260–270.
"The Berlin Magnetically Shielded Room (BMSR), Section A: Design and Construction," Mager, Biomagnetism, 1981, pp. 51–78.
"Installation of a Biomagnetic Measurement Facility in a Hospital Environment," Bercy et al., Biomagnetism, 1981, pp. 95–106.
"Magnetic Measurement of Cardiac Volume Changes," Katila et al, IEEE Trans. Biomed. Eng., vol. BME-29, No. 1, Jan. 1982, pp. 16–25.
"A Study of the Vector Magnetocardiographic Waveform," Rosen et al, IEEE Trans. Biomed. Eng., vol. BME-22, No. 3, May 1975, pp. 167–174.
"Application of Superconducting Magnetometers to the Measurement of the Vector Magnetocardiogram," Wikswo et al, IEEE Transactions on Magnetics, vol. MAG-13, Jan. 1977, pp. 354–357.

Primary Examiner—Ruth S. Smith
Attorney, Agent, or Firm—Hill, Van Santen, Steadman & Simpson

[57] ABSTRACT

A biomagnetic measuring installation has a chamber formed by a number of spaced layers of mumetal within which a measuring cryostat and a patient support table are disposed. The chamber is contained within a room. The installation is supported on a foundation base, which is in turn seated on a sand bed. The layers of the base of the chamber have recesses therein through which a first set of posts extend from the foundation into the chamber, to which a frame which supports the measuring cryostat is secured. A second set of posts extends from the foundation into the chamber to which the patient support is secured. Mechanical vibrations emanating from the patient, or from an attendant walking on the base of the chamber are transmitted to the measuring cryostat only through the very large and thus inert mass of the foundation base. The same is true for external mechanical jolts. As a result, the measured results have a low sensitivity to mechanical influences.

7 Claims, 1 Drawing Sheet

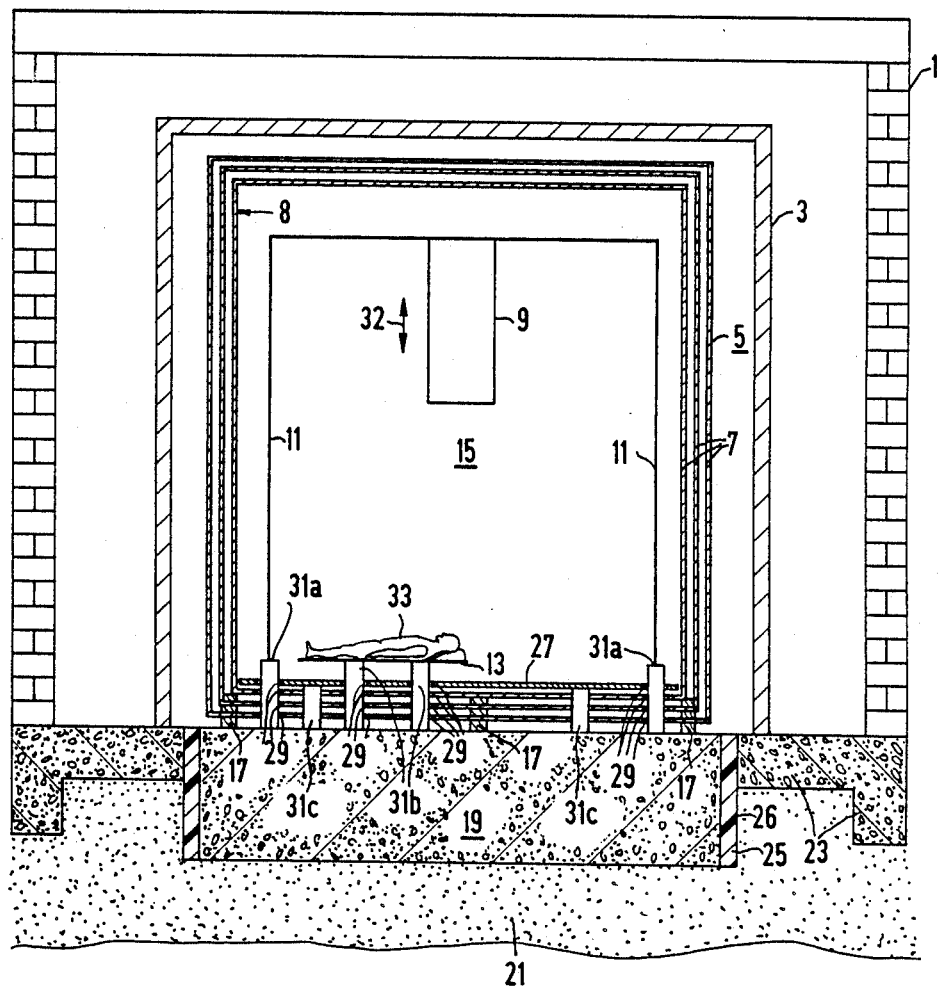

BIOMAGNETIC MEASURING INSTALLATION

BACKGROUND OF THE INVENTION

1. Field of the Invention

The present invention is directed to a biomagnetic measuring installation having a measuring cryostat and a patient support table, the installation being seated on a foundation base.

2. Description of the Prior Art

A very early and thus imperfect measuring installation is described in the article "A Study of the Vector Magnetocardiographic Waveform," by Rosen et al appearing in IEEE Transactions on Biomedical Engineering, Vol. BME-22, No. 3, May 1975 at pages 167–170. In this structure, the patient support and the measuring installation are simply placed on a floor. Such an arrangement, however, results in excessively high noise signals due to mechanical vibration.

A more stable measuring installation is described in "The Berlin Magnetically Shielded Room, Section A: Design and Construction," by Mager appearing in Biomagnetism, 1981. This shielded room is also described in the article "Laesst Hirnstroeme am Magnetfeld messen," by Baier appearing in Elektrotechnik, Vol. 63, No. 24, December 1981 at pages 24–25. This biomagnetic measuring installation, which has a shielding consisting of a number of layers of mumetal is shown on page 74 of the Biomagnetism article. The floor of the measuring chamber is connected to a foundation or base through columns. The cryostat and the patient support are arranged on the floor of the measuring chamber on a stand. In this arrangement, vibrations at the measuring cryostat, which may falsify the measured result, are possible, given movements from outside of the chamber, such as jolts, or movements of the patient within the chamber on the patient support. A movement of the measuring coil by only a few micrometers significantly deteriorates the measured result in the measuring cryostat, which is generally a superconducting Josephson junction magnetometer, also known as SQUID. This is because the measuring coil registers noise signals in addition to the signals from the body of the patient. These noise signals are caused by movements of the measuring coil and the patient relative to each other, or by movements of the measuring coil and the magnetic field of the environment relative to each other. A measuring cryostat of the type under consideration herein is described, for example, in "Biomagnetismus, Signale aus dem Koerper," by Hohnstein in Bild der Wissenschaft, Vol. 8, 1986, page 79.

Various attempts at solving the problem of protecting a biomagnetic measuring installation from vibrations have been proposed in recent years. A satisfactory solution, however, was found.

A vibration shielding chamber is described in "Design, Construction and Performance of a Large-Volume Magnetic Shield," by Kelhae et al, appearing in IEEE Transactions on Magnetics, Vol. MAG-18, No. 1, January 1982 at pages 260–270. The entire chamber is placed on cement blocks. While this has some effect in minimizing vibrations from the exterior of the chamber, vibrations caused inside the chamber (for example, when the patient or the attendant moves) are not suppressed.

Another type of measuring installation is disclosed in "Application of Superconducting Magnetometers to the Measurement of the Vector Magnetocardiogram," Wikswo Jr. et al, IEEE Transactions on Magnetics, Vol. MAG-13, No. 1, January 1977, pages 354–357. This installation is resiliently suspended together with the measuring cryostat and the patient support. A magnetically shielded room is described in "Installation of a Biomagnetic Measurement Facility in a Hospital Environment," Bercy, Biomagnetism 1981 at page 105. The magnetically shielded room is supported on the foundation by damping elements. The room is thus elastically seated, and thus produces an increase in vibrations in the region of the resonant frequency, and a reduction in vibrations above the $\sqrt{2}^{th}$ resonant frequency. Very low resonant frequencies currently obtainable are in the range between 1 and 5 Hz. An oscillatory increase at low frequencies can therefore occur on the basis of frequency components due to external jolts or due to movements of the patient, such as heart activity or breathing activity of the patient.

It is preferable to mount the cryostat as rigidly as possible. This is because the cryostat must be disposed immediately above the patient. If damping elements, such as pneumatic dampers, are used to mount the cryostat, such damping elements may fail. The cryostat is filled with liquid helium, and has a very thin walled base adjacent the patient. If the cryostat should come into contact with the patient, this would constitute a considerable risk for the patient.

SUMMARY OF THE INVENTION

It is an object of the present invention to provide a biomagnetic measuring installation of the type described above wherein mechanical jolts external to the measuring installation of the type encountered in normal day-to-day operation, and vibrations caused by the patient or an attendant inside the chamber have minimal influence on the measuring cryostat in the chamber.

The present invention is based upon the recognition that the effect of vibrations due to such jolts and patient or attendant movement can be considerably reduced if transmitted to the measuring cryostat through a large mass.

In accordance with the principles of the present invention, therefore, a biomagnetic measuring installation is disclosed wherein the measuring cryostat and the patient support are each separately firmly secured to a foundation base through their own connecting means, and wherein the foundation base has a large mass.

In this structure, movements of the patient are necessarily transmitted to the foundation base, which usually weighs between 10 and 20 tons, and are transmitted from the foundation base to the measuring cryostat. This means that the heart and/or respiratory movement of the patient must first excite a mass of several tons and place it in motion before a noticeable influence on the quiescent position of the measuring cryostat can arise. Other internal or external mechanical disturbances, for example produced by street traffic, can similarly only be transmitted to the measuring cryostat by exciting the heavy mass of the foundation base. Since such a heavy mass is difficult to excite, a correspondingly low influence on the measuring cryostat (for example, a SQUID system) results.

DESCRIPTION OF THE DRAWINGS

The single FIGURE is a side sectional view of a biomagnetic measuring installation constructed in accordance with the principles of the present invention.

DESCRIPTION OF THE PREFERRED EMBODIMENTS

A biomagnetic measuring installation generally referenced at 5 is disposed within a room 1, and is surrounded by an enclosure 3. The outside wall of the room 1 may, for example, be masonry, and the enclosure 3 may consist of rigid plaster sheets or sound-damping material. The room 1 and the enclosure 3 serve the principal purpose of protecting measuring installation 5 from vibration or mechanical damage from the exterior.

The measuring installation 5 includes a plurality of intermediate walls or layers 7 consisting of mumetal, which form a chamber or housing 8. The installation 5 also includes a measuring cryostat 9 which is suspended above a patient on a frame or stand 11, and a patient support 13. The chamber 8 defines a measuring volume 15 which is magnetically shielded by the mumetal layers 7. The chamber 8 is connected as rigidly as possible to a heavy foundation base 19 via one or more mounts 17. The mass of the foundation base 19 may be approximately 10 through 20 tons, and may consist of iron-free cement.

Instead of being equipped with the magnetically shielding chamber 8, the measuring installation 5 may be provided with a compensation coil which is accommodated in the measuring cryostat 9 together with the measuring coil.

The cuboid foundation base 19 rests on a sand bed 21. The room 3 has a room foundation 23 which includes a base plate mechanically separated from the foundation 19 by a clearance 25. The clearance 25 may be filled with an expanded plastic 26. This assures that mechanical vibrations from the exterior of the room 3 produced, for example, by street traffic, are not transmitted directly to the foundation base 19.

The chamber 8 includes a base plate 27 which is attached to the innermost layer 7. The portions of the layers 7 at the bottom of the chamber 8, and the bottom plate 27, each have a plurality of holes 29 in registry through which a first set of posts 31a and a second set of posts 31b extend. The posts 31a and 31b consist of an electrically insulating material, such as, for example, wood, ceramic, or plastic. The posts have their respective lower ends anchored rigidly in the foundation base 19, and serve as connecting and supporting elements for components in the interior of the chamber 8.

The stand or frame 11 is attached to the top end of the first set of posts 31a, and the patient support 13 is attached to the second set of posts 31b. The measuring cryostat 9 is height-adjustable within a certain range above the patient support 13. This is indicated by the double arrow 32. Movements of a patient 33 resting on the patient support 13 must therefore first be conducted into the foundation base 19 through the posts 31b before they can be transmitted from the foundation base 19 to the stand 11 via the posts 31a.

As a consequence of the large mass of the foundation 19, movements at the stand 11 and at the measuring cryostat 9 suspended therefrom are largely suppressed. Vibrations exerted on the base plate 27 of the measuring volume 15, for example, due to an attending physician, can likewise be transmitted to the measuring cryostat 9 only through the large mass of the foundation base 19. In order to avoid transmission of such vibrations from the base plate 27 to the layers 7, it is also possible to directly connect the base plate 27 to the foundation via a third set of posts 31c. An extremely high insensitivity of the measuring installation 5 to mechanical disturbances is thereby achieved.

Although modifications and changes may be suggested by those skilled in the art it is the intention of the inventor to embody within the patent warranted hereon all changes and modifications as reasonably and properly come within the scope of his contribution to the art.

I claim as my Invention:

1. A biomagnetic measuring installation comprising:
   a foundation base having a mass in the range of from about 10 tons to about 20 tons;
   a chamber having walls consisting of a plurality of spaced layers of mumetal;
   means for rigidly supporting said chamber on said foundation base;
   a patient support table disposed in said chamber;
   a measuring cryostat disposed in said chamber;
   means for supporting said measuring cryostat in said chamber above said patient support table;
   a first set of posts extending through said chamber rigidly connecting said patient support table to said foundation base; and
   a second set of posts extending through said chamber and rigidly connecting said means for supporting said measuring cryostat to said foundation base, said first and second sets of posts being separate so that any mechanical vibrations must be transmitted between said measuring cryostat and a patient on said patient support table through said foundation mass.

2. A measuring installation as claimed in claim 1, further comprising a sand bed on which said foundation base is seated.

3. A measuring installation as claimed in claim 1, wherein said posts consist of electrically insulating material.

4. A biomagnetic measuring installation as claimed in claim 1, wherein said means for supporting said measuring cryostat comprises means for adjusting the height of said measuring cryostat relative to said patient support table.

5. A biomagnetic measuring installation as claimed in claim 1, wherein said chamber has a base plate, and further comprising a third set of posts rigidly connecting said base plate to said foundation base.

6. A biomagnetic measuring installation as claimed in claim 1, further comprising a room surrounding said chamber and a room foundation supporting said room, said room foundation being spaced from said base foundation.

7. A biomagnetic measuring installation as claimed in claim 6, further comprising an enclosure consisting of sound-damping material surrounding said chamber within said room.

* * * * *